Figure 1:
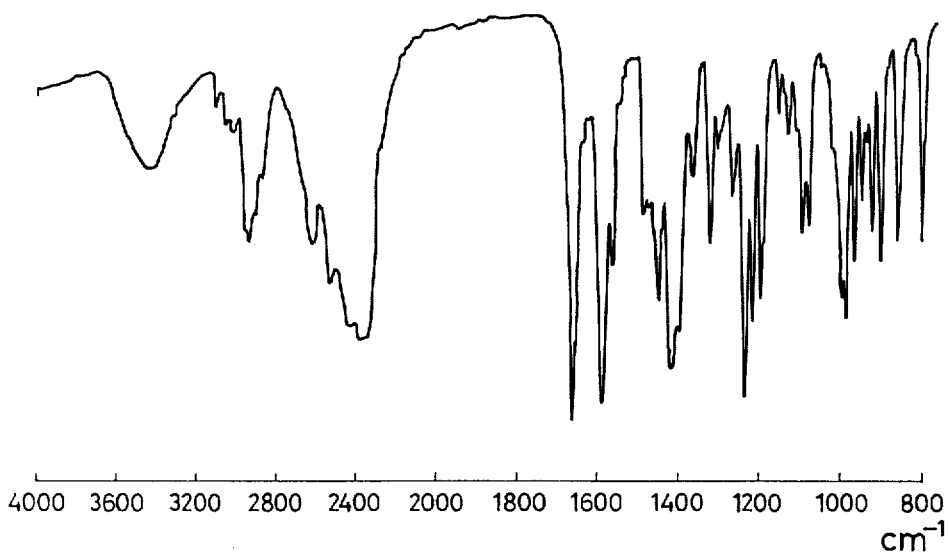

United States Patent [19]
Yamada et al.

[11] 3,933,918
[45] Jan. 20, 1976

[54] 2-ALLYLOXY-4-CHLORO-ACETOPHENONE

[75] Inventors: Arihiro Yamada, Takaishi; Kyoichi Fujii, Sakai, both of Japan

[73] Assignee: Kyowa Hakko Kogyo Co., Ltd., Tokyo, Japan

[22] Filed: Sept. 3, 1974

[21] Appl. No.: 502,776

[30] Foreign Application Priority Data
Sept. 4, 1973    Japan................................ 48-98923

[52] U.S. Cl............ 260/592; 260/293.8; 260/473 R; 260/544 M; 424/267
[51] Int. Cl.$^2$............................................ C07C 49/78
[58] Field of Search.......................... 260/293.8, 592

[56] References Cited
UNITED STATES PATENTS
2,771,391    11/1956    Bockstahler..................... 260/293.8

OTHER PUBLICATIONS

C.A. 70:37,779 g (1969) Serper.

Name Reactions Organic Organic Chemistry (1954) Academic Press Inc. — Surrey.

J. Indian Chem. Soc. 34:830–832 (1957), Tiwari et al.

Primary Examiner—Sherman D. Winters
Attorney, Agent, or Firm—Fitzpatrick, Cella, Harper & Scinto

[57] ABSTRACT

2-Allyloxy-4-chloro-$\beta$-piperidinopropiophenone is prepared by reacting 2-allyloxy-4-chloroacetophenone with piperidine and formaldehyde. 2-Allyloxy-4-chloro-$\beta$-piperidinopropiophenone is useful as an antitussive.

1 Claim, 4 Drawing Figures

2-ALLYLOXY-4-CHLORO-ACETOPHENONE

BACKGROUND OF THE INVENTION

This invention relates to 2-allyloxy-4-chloro-β-piperidinopropiophenone and to a process for producing same. 2-Allyloxy-4-chloro-β-piperidinopropiophenone shows a strong antitussive action.

Heretofore, various antitussives, either centrally acting or peripherally acting, have been proposed. However, there have been no reports on antitussives which act on both central nerve and peripheral nerve at a usual effective dose.

2-Allyloxy-4-chloro-β-piperidinopropiophenone of the present invention has been found to act not only centrally but also peripherally, particularly on the pulmonary stretch receptor. Therefore, the compound is expected to be useful as a new type of an antitussive.

2-Allyloxy-4-chloro-β-piperidinopropiophenone which is the subject of the present invention is a new compound and has the formula:

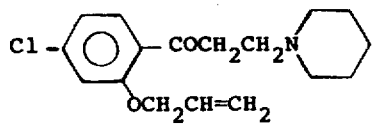

The compound is usually employed in the form of a pharmaceutically acceptable salt. Suitable salts are the acid addition salts such as, for example, the salts of inorganic acids such as the hydrochloride, hydrobromide and sulfate and the organic acid salts such as the maleate, fumarate, citrate, tartrate and succinate.

DESCRIPTION OF THE INVENTION

In accordance with the present invention, the desired 2-allyloxy-4-chloro-β-piperidinopropiophenone is prepared by condensation of 2-allyloxy-4-chloroacetophenone with piperidine and formaldehyde. Such condensation reaction is known as Mannich reaction. The reaction is schematically shown as follows.

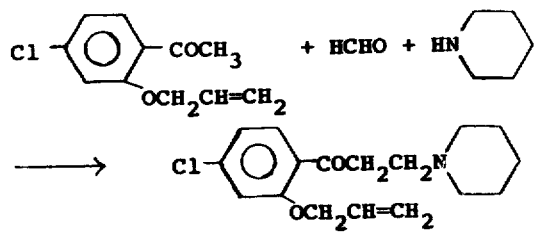

2-Allyloxy-4-chloroacetophenone which is the starting compound for the preparation of 2-allyloxy-4-chloro-β-piperidinopropiophenone is also a new compound. The compound is prepared, for example, by O-allylating 2-hydroxy-4-chloroacetophenone. The compound is also prepared by simultaneous hydrolyzation and decarboxylation of 2-allyloxy-4-chlorobenzoylmalonate which is prepared from 2-allyloxy-4-chlorobenzoylchloride and magnesium derivative of malonate. Of course, it is to be understood that the compound may further be prepared by any of other known methods.

Describing the preparation of 2-allyloxy-4-chloroacetophenone more in detail, the compound is prepared by reacting 2-hydroxy-4-chloroacetophenone with an allylating agent in a solvent in the presence of an acid binding agent.

2-Hydroxy-4-chloroacetophenone can be prepared according to any of the methods known in the art, for example, the method of Pawar et al. [Pawar, R.A., et al: Indian Journal of Chemistry, Vol. 8, pp. 522–528 (1970)].

As the allylating agent, allyl halides such as allyl chloride and allyl bromide and allyl sulfonates such as allyl p-toluenesulfonate, allyl benzenesulfonate and allyl methanesulfonate may be used.

Any acid-binding agent that reacts with 2-hydroxy-4-chloroacetophenone to form the phenolate may be used. For example, alkaline carbonate such as sodium carbonate and potassium carbonate, alkaline bicarbonate such as sodium bicarbonate and potassium bicarbonate and alkali hydroxide such as sodium hydroxide and potassium hydroxide may be mentioned.

As the solvent, polar solvents such as methanol, ethanol, butanol, acetone, methyl ethyl ketone and water and mixtures thereof may be used.

Reaction is carried out with heating preferably at 40°C to a reflux temperature of the solvent. The reaction time varies depending upon the reaction conditions, for example, the kind and the amount of solvents to be used, reaction temperature, etc. but usually the reaction is complete in several hours.

After the completion of reaction, the reaction mixture is subjected to filtration. The filtrate is concentrated and cooled to give crude crystals. The cyrstals are separated by filtration, washed and dried to obtain crude product of 2-allyloxy-4-chloroacetophenone. In this manner, the crude product of 2-allyloxy-4-chloroacetophenone is obtained in a yield of 85–95%. The thus obtained crude product can be purified by recrystallization from a mixture of methanol and water (1–2:1 by volume).

Alternatively, 2-allyloxy-4-chloroacetophenone is prepared from 2-allyloxy-4-chlorobenzoylchloride. In this method, 2-allyloxy-4-chlorobenzoylchloride is reacted with magnesium derivative of malonate to prepare 2-allyloxy-4-chlorobenzoylmalonate, which is then converted to 2-allyloxy-4-chloroacetophenone by simultaneous elimination of alkyl group and carbon dioxide.

More specifically, first, 2-allyloxy-4-chlorobenzoylchloride is reacted with magnesium derivative of malonate.

2-Allyloxy-4-chlorobenzoylchloride can be prepared from p-aminosalicylic acid in a known manner (Japanese patent publication No. 13857/1965) through several steps of reactions.

Usually, the magnesium derivative of malonate is prepared by reacting malonate with metal magnesium in the presence of ethanol, but the product can, of course, be prepared according to any of other known methods. As the malonate, dimethylmalonate and diethylmalonate are suitable for an industrial operation.

Reaction of 2-allyloxy-4-chlorobenzoylchloride and the magnesium derivative of malonate is carried out in an organic solvent such as ether, etc. usually with heating at 30° to 50°C for half an hour to 3 hours. After the completion of reaction, the reaction mixture is neutralized with a dilute acid such as sulfuric acid. The mixture is separated into a water layer and an organic solvent layer. The water layer is extracted with the same organic solvent. The organic solvent layer and the organic solvent extract are combined and washed with water. After removing the solvent by distillation under reduced pressure, 2-allyloxy-4-chlorobenzoylmalonate is obtained.

Then, 2-allyloxy-4-chlorobenzoylmalonate prepared above is converted to 2-allyloxy-4-chloroacetophenone by simultaneous hydrolyzation and decarboxylation. Such reaction is carried out in an aqueous medium at 40°C to a reflux temperature of the solvent in the presence of an acid such as acetic acid, sulfuric acid, etc. Generally, the reaction is complete in 4 to 24 hours.

After the completion of reaction, the reaction mixture is cooled and neutralized with an alkaline solution such as an aqueous solution of sodium hydroxide. The mixture is then extracted with an organic solvent such as ether and benzene. The extract is dried with anhydrous sodium sulfate and the solvent is distilled off to give crude crystals of 2-allyloxy-4-chloroacetophenone. The crystals are separated by filtration. The total yield corresponds to 85–95%.

It is to be understood that in the above-described method, similar results can be obtained when compounds functionally equivalent to malonate such as cyanoacetate are used in place of malonate.

Now, describing more in detail the preparation of 2-allyloxy-4-chloro-$\beta$-piperidinopropiophenone which is the desired compound of the present invention, the compound is prepared by condensing 2-allyloxy-4-chloroacetophenone with piperidine and formaldehyde.

2-Allyloxy-4-chloroacetophenone can be prepared in a manner such as described above. As the reactant formaldehyde, the use of paraformaldehyde is preferred but an aqueous solution of formaldehyde may also be used. Further, it is preferred to use a mineral acid salt form of piperidine, such as piperidine hydrochloride, etc.

Generally, 1.0–1.2 mols of piperidine and 1.0–2.0 mols of formaldehyde are used per 1 mol of 2-allyloxy-4-chloroacetophenone.

Reaction is carried out in a solvent. Suitable solvents are polar solvents, for example, alcohols such as ethanol, etc. and nitromethane.

Reaction is carried out with heating generally at 40°C to a reflux temperature under a strongly acidic condition in the presence of a strong acid such as hydrochloric acid, etc. Reaction is complete in one to several hours. In order to obtain a high yield of the product, water formed during the reaction is removed by azeotropic distillation in mixture with, for example, benzene, hexane or toluene.

After the completion of reaction, the resulting reaction mixture is cooled to room temperature. To the mixture is then added an appropriate precipitant such as ether, benzene and cyclohexane to give crude crystals of the desired compound. The crude crystals are separated by filtration, washed with an organic solvent such as ether and dried. Thus, crude product of 2-allyloxy-4-chloro-$\beta$-piperidinopropiophenone is obtained in an acid salt form such as hydrochloride, etc. in a yield of 80–90%. The crude crystals can be purified by recrystallization from water or alcohols.

According to the above procedures, the desired compound is obtained in the form of an acid addition salt. The product may be converted into the free form in a conventional manner. For example, the compound in the salt form is dissolved in water and the pH of the solution is adjusted to 8.0–11.0, preferably 9.0–10.0 with an alkali such as caustic soda. The solution is subjected to an extraction with an organic solvent such as ether, benzene, etc. The solvent is distilled off to produce the compound in the free form. Further, where an acid addition salt other than the one obtained is desired, to the above-mentioned organic solvent extract of the free form compound is added a solution of the desired acid in an organic solvent such as ether, alcohol and water. The mixture is concentrated and to the concentrate is added an appropriate precipitant such as acetone, ethyl acetate and benzene to give crystals. The crystals are separated by filtration, washed and dried. In this manner, an acid addition salt of the compound can be obtained.

2-Allyloxy-4-chloro-$\beta$-piperidinopropiophenone and its acid addition salts are found to have antitussive activity. The pharmacological action of the compounds is apparent from the following experiments. In each test, 2-allyloxy-4-chloro-$\beta$-piperidinopropiophenone hydrochloride is used as the test compound and codeine phosphate, a well-known antitussive is used as a standard compound.

EXPERIMENT I

Acute Toxicity in Mice and in Rats — Determined as $LD_{50}$ a. More than 5 groups of male ddy-strain mice, each consisting of 10 animals weighing 18–20 g are used. The animals are given graded doses of the test compound or the standard compound by subcutaneous injection and are observed for 72 hours.

b. More than 6 groups of male dd-strain mice, each consisting of 20 animals weighing 18–20 g are used. The animals are given graded doses of the test compound or the standard compound orally and are observed for one week.

c. More than 5 groups of male Wistar strain rats, each consisting of 15 animals weighing 110–150 g are used. The animals are given graded doses of the test compound and the standard compound orally and are observed for one week.

The $LD_{50}$ is calculated according to the method of Litchfield and Wilcoxon [J. Pharmacol. & Exper. Therap. 96, 99 (1949)].

The results are shown in Table 1 below.

Table 1

| Drug | $LD_{50}$ (mg/kg) | | |
|---|---|---|---|
| | a) Mouse (S.C.) | b) Mouse (P.O.) | c) Rat (P.O.) |
| 2-Allyloxy-4-chloro-$\beta$-piperidinopropiophenone hydrochloride | 105 | 240 | 1,025 |
| Codeine phosphate | 191 | 729 | 807 |

EXPERIMENT II

Antitussive Effect a. Effect on coughs induced by mechanical stimulation of the tracheal mucosa in dogs More than 4 groups of dogs, each consisting of 5 animals of either sex weighing 6–10 kg are used. The test is conducted according to "Coughing dog" method [Jap. J. Pharmacol. 2, 7–13 (1952); Pharm. Bull. (Japan) 2, 298 (1954); and Jap. J. Pharmacol. 4, 130 (1955)]. Coughs are induced by mechanical stimulation with a bristle stimulator made of pig bristles on the tracheal bifurcation through a chronically-built tracheal fistula.

Stimulation is applied by constantly and intensely moving the stimulator up and down 10 times for 20 seconds and the stimulation is repeated every 5 minutes. The changes of the inner pressure of the trachea brought about by coughs are recorded on a smoked paper. The animals are given graded doses of the test compound or the standard compound by intravenous injection.

The antitussive effect of the compounds is determined by the changes in both the amplitude and frequency of the cough curves on the smoked paper and the duration of such changes. When the amplitude and/or the frequency are decreased by more than 20% as compared with those before administration of the drug and when the decrease lasts for more than 20 minutes, the effect is determined to be significant. On the basis of the criteria of evaluation, the 50% antitussive dose (hereinafter referred to as $AtD_{50}$) is calculated according to the method of Litchfield and Wilcoxon.

b. Effect on coughs induced by mechanical stimulation of the tracheal mucosa in anesthetized cats More than 4 groups of cats, each consisting of 6 animals of either sex weighing 2–3 kg are used. The animals are lightly anesthetized by intraperitoneal injection of 20 mg/kg of pentobarbital sodium. The test is conducted according to "Coughing cat" method [Folia Pharmacol japon. 55 99 (1959)].

Coughs are induced in the same manner as described above except that a bristle stimulator made of whiskers of rabbit is used. The $AtD_{50}$ is calculated in the same manner as described above.

c. Effect on coughs induced by electrical stimulation of central stump of the superior laryngeal nerve in anesthetized cats More than 4 groups of cats, each consisting of 6 animals of either sex weighing 2–3 kg are used. The animals are lightly anesthetized by intraperitoneal injection of 20 mg/kg of pentobarbital sodium. The test is conducted according to the method of Domenjoz (Arch. Exp. Path. u. Pharmakol, 215, 19 (1952)].

Coughs are induced by electrically stimulating the central stump of the superior laryngeal nerve under the following conditions: wave, rectangular wave; pulse duration, 1 msec.; frequency, 5–10 cps.; voltage, 0.5–1.5 Volt; and duration of stimulation, 10 sec. The changes of inner pressure of the trachea brought about by coughs are recorded. The animals are given graded doses of the test compound or the standard compound by intravenous injection.

The antitussive effect of the compounds is determined by the changes in both the amplitude and frequency of the cough curves and the duration of the changes. When the amplitude and/or the frequency of the coughs induced by a stimulus of moderate intensity are decreased by more than 20% as compared with those before administration of the drug and when the decrease lasts for more than 20 minutes, the effect is determined to be significant. On the basis of the criteria of evaluation, the $AtD_{50}$ is calculated according to the method of Lichfield and Wilcoxon.

The results of the above three tests are shown in Table 2 below.

Table 2

| Drug | $AtD_{50}$ (mg/kg i.v.) | | |
|---|---|---|---|
| | Dog Mechanical stimulation | Cat Mechanical stimulation | Cat Electrical stimulation |
| 2-Allyloxy-4-chloro-$\beta$-piperidino-propiophenone hydrochloride | 3.3 (2.8–3.6)* | 4.8 (3.9–5.8) | 4.2 (3.6–4.9) |
| Codeine phosphate | 2.5 (2.3–2.7) | 2.3 (1.9–2.6) | 2.1 (1.6–2.7) |

*The values within the parentheses indicate the fiducial limits. (Significance: P = 0.05)

From the results of the above experiments, it can be seen that the hydrochloride of 2-allyloxy-4-chloro-$\beta$-piperidinopropiophenone shows an antitussive effect equal to codeine phosphate in dogs and cats.

Further, the following experiments are conducted to examine the sites of antitussive action of the compound.

EXPERIMENT III a. Comparison of equi-active doses for various routes of administration Five dogs weighing 8–10 kg are used. Polyethylene tubes are previously installed in the animals in the femoral vein, the vertebral artery and the cerebello-medullary cistern. The animals are lightly anesthetized by intraperitoneal injection of 20 mg/kg of pentobarbital sodium. The hydrochloride of 2-allyloxy-4-chloro-$\beta$-piperidinopropiophenone is given through the polyethylene tubes. Coughs are induced by mechanical stimulation on the mucosa of the tracheal bifurcation. The doses necessary to obtain the same degree of antitussive effect as that obtained by the administration through the femoral vein are determined.

Nearly the same antitussive effect is obtained by the following doses (mg/kg):

Femoral vein:vertebral artery:cerebello-medullary cistern = 4.30:0.4–0.8:0.06–0.1.

Where the dose through the femoral vein is taken as 1.0, the ratio is 1:1/5–1/10:1/40–1/65.

When the same test is conducted using codeine phosphate which is known as a centrally acting antitussive, the ratio of 1:1/8–1/12:1/50–1/80 is obtained.

As shown by the above experiment results, the ratio of the effective doses for the three administration routes obtained by using the present compound is almost the same as that obtained by using codeine. Thus, it is understood that the present compound exerts its action on the central nerve.

b. Effect on the pulmonary stretch receptor impulses

Five guinea pigs weighing 400–600 g are used. The animals are anesthetized by subcutaneous injection of 1.2 g/kg of urethane and disposed in a supine position. The chest is opened under artificial ventilation. The left vagus nerve is sectioned at the cervical region and the peripheral stumps is placed on a bipolar platinum electrode. The impulses from the pulmonary stretch receptors are observed on an oscilloscope and recorded with a long-recording camera.

The animals are given graded doses of the hydrochloride of 2-allyloxy-4-chloro-$\beta$-piperidinopropiophenone by intravenous injection.

The action of the compound on a peripheral nerve is determined by the change of the voltage of the stretch receptor impulses.

As a control, the same test is conducted using benzonatate which is known as a peripherally acting antitussive.

The results are shown in Table 3 below.

Table 3

| Drug | Dose (mg/kg) | Change of voltage of stretch receptor impulses (as compared with that before treatment with drug) | Time required to return to the level before treatment with drug (min.) |
|---|---|---|---|
| 2-Allyloxy-4-chloro-β-piperidino-propiophenone hydrochloride | 1.0–2.0 | none | |
| | 5.0 | reduced to ½–¾ | 10–20 |
| | 10.0 | reduced to ½ | about 30 |
| Benzonatate | 0.1–0.5 | none | |
| | 1.0 | reduced to ¾ | 10 |
| | 2.0 | reduced to less than ½ | 30 |
| | 4.0 | reduced to zero | 30–40 |

From the experiment results, it can be seen that the effect of the present compound is to repress the impulses of the pulmonary stretch receptor.

Thus, it is concluded that 2-allyloxy-4-chloro-β-piperidinopropiophenone of the invention acts centrally but it also exerts a considerable action on peripheral nerves.

2-Allyloxy-4-chloro-β-piperidinopropiophenone may be administered orally in an appropriate form such as tablet, powder and syrup at a dose of about 25 mg–50 mg per day.

The present invention is further illustrated by the following representative examples.

EXAMPLE 1

2-Allyloxy-4-Chloroacetophenone 15.2 g of anhydrous potassium carbonate is suspended in 50 ml of acetone. To the suspension is added 17.0 g of 2-hydroxy-4-chloroacetophenone. To the mixture is added dropwise 13.2 g of allyl bromide while refluxing. After 6 hours of reaction, the precipitates formed are removed by filtration and the filtrate is concentrated under reduced pressure. As the result, 18.3 g of 2-allyloxy-4-chloroacetophenone is obtained in a yield of 87%. Melting point: 69°–70°C.

Figure 3:
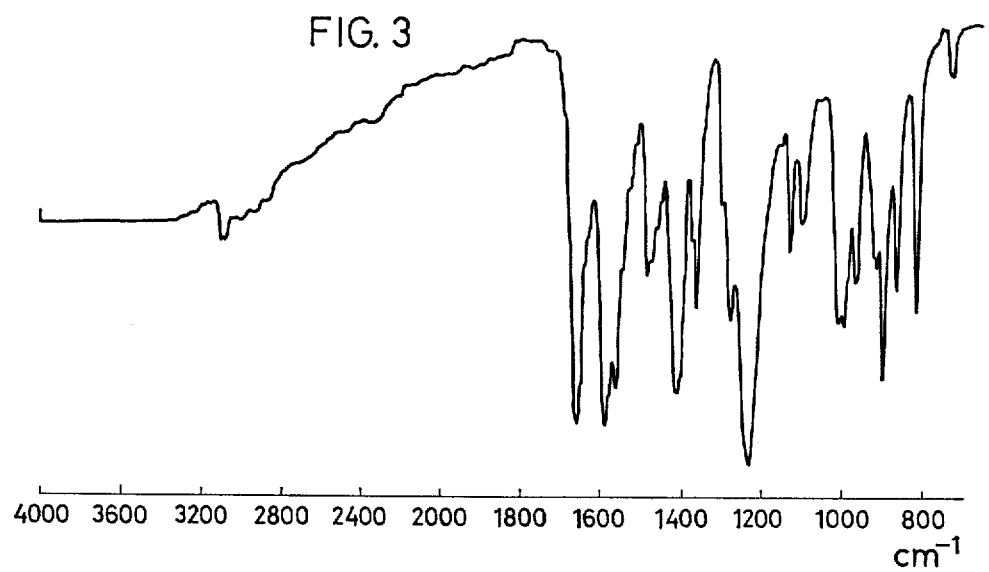
Figure 4:
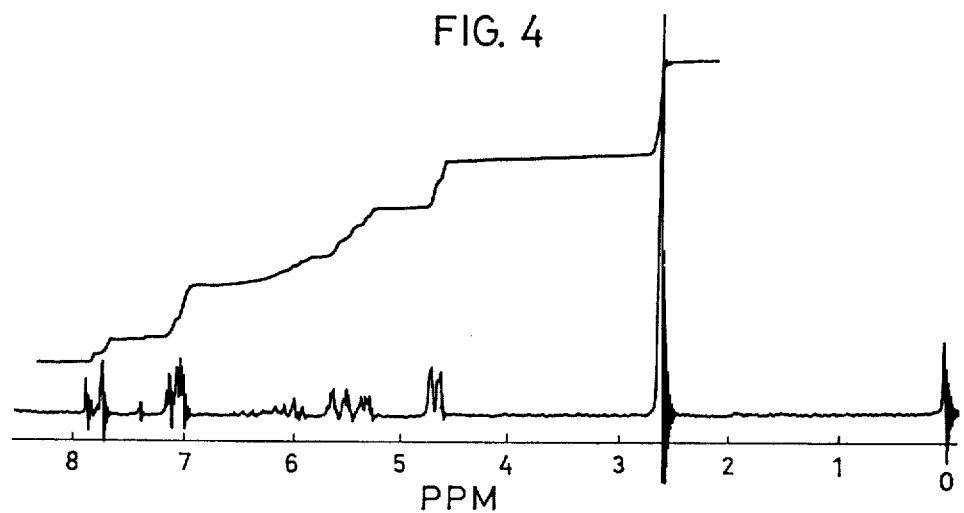

Elementary analysis:
Calculated for $C_{11}H_{11}O_2Cl$: C = 62.71%; H = 5.26%: Cl = 16.83%
Found: C = 62.53%; H = 5.33%; Cl = 16.80%
IR spectrum: shown in FIG. 3
NMR spectrum: shown in FIG. 4

2-Allyloxy-4-Chloro-β-Piperidinopropiophenone Hydrochloride 7.5 g of paraformaldehyde, 29.5 g of piperidine hydrochloride and 51.2 g of 2-allyloxy-4-chloroacetophenone are dissolved in 100 ml of nitromethane. To the solution are added 15 ml of absolute alcohol, 30 ml of toluene and 1 ml of concentrated hydrochloric acid. The mixture is refluxed with heating for about one hour while removing water by azeotropic distillation. After the completion of reaction, the mixture is cooled to room temperature. To the mixture is added 1 l of ether to give crude crystals. The crystals are separated by filtration, washed with ether and dried. Thus, 67.3 g of crude crystals are obtained. The crystals are then subjected to recrystallization from 270 ml of water and dried under reduced pressure. As the result, 59.2 g of the hydrochloride of 2-allyloxy-4-chloro-β-piperidinopropiophenone is obtained in a yield of 71%. Melting point: 133°–135°C.

Elementary analysis: Calculated for $C_{17}H_{23}NO_2Cl_2$: C = 59.31%; H = 6.73%: N = 4.07%: Cl = 20.60%.
Found: C = 59.22%: H = 7.02%: N = 4.18%; Cl = 20.68%.

Figure 2:
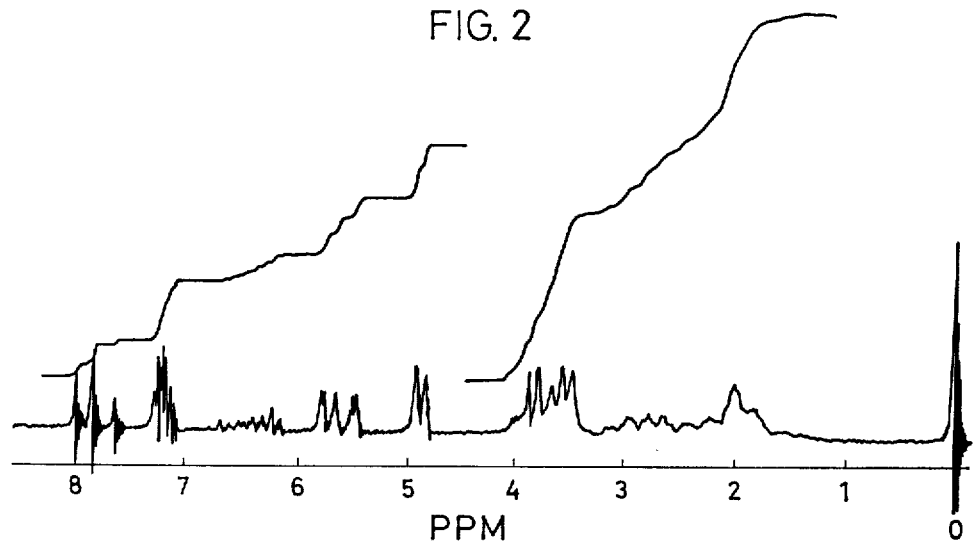

IR spectrum: shown in FIG. 1.
NMR spectrum: shown in FIG. 2.

EXAMPLE 2

2-Allyloxy-4-Chlorobenzoyldiethylmalonate 4.9 g of magnesium and 4.5 ml of ethanol are mixed and to the mixture are added 0.5 ml of carbon tetrachloride and then 136 ml of ether. To the resulting mixture is added a mixture of 31.9 g of diethylmalonate, 18.1 ml of ethanol and 22.6 ml of ether while refluxing. After two hours of reflux, a solution of 42 g of 2-allyloxy-4-chlorobenzoylchloride in 45.2 ml of ether is added dropwise to the reaction mixture and the mixture is refluxed for one hour further. After the completion of reaction, the mixture is cooled. To the mixture is then added a dilute sulfuric acid prepared by diluting 22.6 g of concentrated sulfuric acid with 181 ml of water, while cooling the mixture with ice water. The mixture is separated into a water layer and an ether layer. The water layer is extracted with 70 ml of ether. The ether layer and the ether extract are combined and washed with 100 ml of water. Ether is distilled off under reduced pressure. As a result, 64 g of 2-allyloxy-4-chlorobenzoyldiethylmalonate is obtained as an oily matter.

2-Allyloxy-4-Chloroacetophenone 64 g of 2-allyloxy-4-chlorobenzoyldiethylmalonate is added to a mixture of 55 ml of acetic acid, 6.9 ml. of concentrated sulfuric acid and 36 ml of water. The mixture is refluxed with heating for 22 hours. The mixture is then cooled and neutralized with 170 ml of an aqueous 20% sodium hydroxide solution. The resulting mixture is extracted for three times each with 100 ml of ether. The ether extract is dried with anhydrous sodium sulfate and ether is distilled off. As the result, 33.1 g of light yellow crystals are obtained in a yield of 87%. Melting point: 69°–70°C.

2-Allyloxy-4-Chloro-β-Piperidinopropiophenone 3.7 g of paraformaldehyde, 14.8 g of piperidine hydrochloride and 25.6 g of 2-allyloxy-4-chloroacetophenone are used as the starting meterials and the procedure to prepare 2-allyloxy-4-chloro-β-piperidinopropiophenone described in Example 1 is repeated. As a result, 29.0 g of the hydrochloride of 2-allyloxy-4-chloro-β-piperidinopropiophenone is obtained in a yield of 70%.

Melting point: 133°–134°C.

Elementary analysis: Calculated for $C_{17}H_{23}NO_2$ $_2$: C = 59.31%; H = 6.73%; N = 4.07%; Cl = 20.60%.
Found: C = 59.13%; H = 6.92%; N = 4.21%; Cl = 20.72%.

12.3 g of the thus obtained product is dissolved in 100 ml of water. The solution is adjusted to a pH of 9.9 with sodium hydroxide and extracted with 100 ml of ether. The ether layer is dried with anhydrous sodium sulfate and ether is distilled off. As the result, 7.4 g of 2-allyloxy-4-chloro-β-piperidinopropiophenone is obtained in a yield of 66%. Boiling point: 135°–140°C/0.7 mmHg.

Elementary analysis: Calculated for $C_{17}H_{22}NO_2Cl$: C = 66.33%; H = 7.21%; N = 4.55%; Cl = 11.52%.

Found: C = 66.19%; H = 7.50%; N = 4.32%; Cl = 11.50%.

What is claimed is:
1. A compound of the formula:

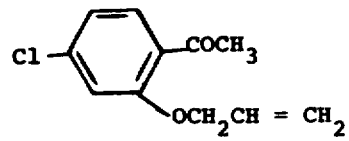

* * * * *

UNITED STATES PATENT OFFICE
CERTIFICATE OF CORRECTION

Patent No. 3,933,918              Dated   JANUARY 20, 1976

Inventor(s)   ARIHIRO YAMADA, ET AL

It is certified that error appears in the above-identified patent and that said Letters Patent are hereby corrected as shown below:

Column 8, line 68, "$C_{17}H_{23}NO_2$" should read

--$C_{17}H_{23}NO_2Cl_2$:--

Column 9, line 1, "$_2$:C=59.31%:" should read

--C=59.31%:--

Signed and Sealed this twenty-seventh Day of April 1976

[SEAL]

Attest:

RUTH C. MASON
*Attesting Officer*

C. MARSHALL DANN
*Commissioner of Patents and Trademarks*